United States Patent [19]

Barfurth et al.

[11] Patent Number: 4,931,094
[45] Date of Patent: Jun. 5, 1990

[54] TITANIUM(IV)-CHELATES AND THEIR USE IN PRINTING INKS

[75] Inventors: Dieter Barfurth, Troisdorf-Spich; Claus Lindzus, Cologne; Heinz Nestler, Troisdorf-Eschmar, all of Fed. Rep. of Germany

[73] Assignee: Huels Troisdorf AG, Troisdorf, Fed. Rep. of Germany

[21] Appl. No.: 252,700

[22] Filed: Oct. 3, 1988

[30] Foreign Application Priority Data

Oct. 5, 1987 [DE] Fed. Rep. of Germany ....... 3733608

[51] Int. Cl.$^5$ ............................................. C09D 11/00
[52] U.S. Cl. ...................................... 106/20; 106/22; 556/55
[58] Field of Search ...................... 106/287.19, 20, 22, 106/447; 556/40, 54, 55

[56] References Cited

U.S. PATENT DOCUMENTS

| | | | |
|---|---|---|---|
| 2,966,505 | 12/1960 | Lane | 556/55 |
| 3,090,728 | 5/1963 | Berger | 556/55 |
| 3,387,994 | 6/1968 | Dunton | 556/55 |
| 3,682,688 | 8/1972 | Hughes | 106/27 |
| 4,113,757 | 9/1978 | Kay | 556/55 |
| 4,617,408 | 10/1986 | Nestler | 106/447 |

OTHER PUBLICATIONS

Chem. Abst. 79:43090c Pomogailo, 1973.
"Synthesis, characterization, and structural studies of gallium citrate complexes", Banta et al., CAN. J. Chem. vol. 63, 1985, pp. 2545-2549.

Primary Examiner—Theodore Morris
Attorney, Agent, or Firm—Felfe & Lynch

[57] ABSTRACT

Novel alkoxy titanium(IV)-chelates are used to modify printing inks based on nitrocellulose or other cellulose ester derivatives. The novel chelates comprise citric acid alkyl esters as chelate formers. They delay, as other titanium chelates do, the well-known catalytic effect of the titanium component in cross-linking reactions. When used in printing inks, the novel titanium chelates and their alcoholic solutions have the advantage that they have an insignificant color of their own, so that they practically do not discolor the printing inks. A further advantage of the novel chelates resides in that they do not enter into alteration effects with antioxidants based on phenol, so that they can also be used for printing inks which are to be applied to polymeric substrates containing such antioxidants without the occurence of discoloration.

5 Claims, No Drawings

TITANIUM(IV)-CHELATES AND THEIR USE IN PRINTING INKS

FIELD OF THE INVENTION

This invention relates to titanium(IV)-chelates which are derived from titanic acid esters in that at least one alkoxy group is replaced by a chelate former.

BACKGROUND OF THE INVENTION

Titanium(IV)-chelates in which, for example, acetylacetone is used as the chelate former are known. These titanium acetylacetone-chelates, which are also known as titanium acetylacetonates, are commonly used as additives for flexographic printing inks based on nitrocellulose or cellulose ester derivatives. The cross-linking effects of the titanium component in these chelates is reduced to such an extent that no cross-linking occurs in the printing ink itself; the cross-linking effect occurs only after imprinting of the substrate upon evaporation of the solvent and under the influence of humidity.

However, the titanium acetylacetonates exhibit the following disadvantages when they are used in the above-mentioned printing inks:

Because of their intense reddish brown color, they impart a yellowish tinge to white printing inks. In addition, upon drying on the substrate they often develop an undesirable odor. Furthermore, the above-mentioned discoloration occurs especially in the case of those substrate materials which contain antioxidants based on phenol. Such antioxidants are, for example, contained in polyolefin foils or in heat-sealing substrates, so that printing inks containing titanium acetylacetonates cannot be employed for imprinting such materials without discoloration of the substrate.

OBJECTS OF THE INVENTION

It is an object of the present invention to provide a titanium-chelate in which the cross-linking effect of the titanium component is reduced to the same extent as in titanium acetylacetonates, so that cross-linking and adhesion in compositions modified with these chelates do not take place until during or after the evaporation of the solvent.

It is another object of this invention to provide a titanium-chelate which does not produce any or only very minor discoloration when it is used in printing inks based on cellulose esters.

DESCRIPTION OF THE INVENTION

We have discovered that the above objects are achieved by alkoxy-titanium(IV)-chelates which contain citric acid esters as chelate formers. For use in the above-mentioned printing inks, these titanium-chelates are provided in the form of alcoholic solutions, so that these solutions and their employment in printing inks also constitute fulfillment of the above-mentioned objects.

The alkoxy groups of the novel titanium-chelates contain preferably 2 to 4 carbon atoms; however, for special applications they may also contain up to 8 carbon atoms, inclusive, and they may further be interrupted by oxygen atoms.

The citric acid ester component of the novel chelates is derived from citric acid partial esters, preferably from those citric acid dialkyl esters whose alkyl groups contain preferably 2 to 4 carbon atoms.

In the noval chelates pursuant to the present invention, 1 or 2 of the alkoxy groups of a titanic acid ester may be replaced by the citric acid ester groups previously referred to. Accordingly, the ratio of alkoxy groups bonded with the central titanium atom to citric acid ester groups may range between 1:1 and 3:1. In addition, one or more of the original alkoxy groups may be replaced by other known chelate formers.

The novel titanium-chelates may be prepared in simple manner by reacting a titanic acid ester with an amount of citric acid ester corresponding to the desired end product, and subsequently distilling off the alcohol liberated by the reaction. The reaction is advantageously carried out by adding the titanic acid ester to the citric acid ester which has been pre-heated to the reaction temperature. The reaction temperature lies in the range between 20° and 100° C., preferably between 60° and 80° C. The reaction is, in general, complete after a reaction period of 2 to 5 hours if it is carried out in the preferred temperature range. For the preparation of the pure esters an amount of alcohol is distilled off which corresponds to the amount of citric acid ester provided.

If it is decided to obtain alcoholic solutions of the novel titanium-chelate, it is of course not necessary to distill off the entire amount of alcohol released by the reaction. In that case only so much alcohol is distilled off as is required for the preparation of a ready-to-use chelate. Sometimes no alcohol at all need to be distilled off. The solutions obtained in this manner have a chelate content which is in excess of 80% by weight.

The solutions, which may optionally be further diluted with alcohols or other solvents when used in printing inks, exhibit at least the same, mostly, however, better properties with respect to titanium acetyl acetonate (TiACA). Quantities between 1 and 10, preferably between 1 and 4 wt.-%, referred to the weight of the printing ink, can be admixed without effecting a gel formation of the printing ink and have, however, the ability, to considerably improve the adhesion of the ink to the substrate. The storability of these printing inks is favourable (Example 7) and can be compared such as for an addition of TiACA. When storing for months (usual is only a storage for some weeks) only a slight increase of the viscosity is obtained. (Only a viscosity from 2000 would be critical, but by diluting with small quantities of usual solvent it can be overcome).

The novel titanium chelates of the citric acid are decisively superior compared with TiACA, based on the fact that no discoloration of the printing inks—even not for white printing inks—is effected. TiACA has the disadvantage to discolor printing inks to become yellowish and white inks (TiO$_2$) becoming visibly and remarkably yellow, and up to now no remedy could be found.

The color of the novel chelates is light yellow to yellow. Surprisingly, no discoloration occurs either when these printing inks are applied to substrates which contain phenol-based antioxidants. Printing inks with any addition of the chelates under the invention remain without any odour.

The surprising improvement of printing inks by addition of the novel type of chelates under the invention can be taken from the Table of Example 8. There is shown the remission in percentage in dependence of the wave length λ (100% remission of all wave lengths gives an optic impression of white). TiACA containing white ink has a low remission in the blue range (λ=400–45 nm) and high remission in the red range compared with the samples of comparison. This corresponds to a visible yellow discoloration. White inks containing the Ti-chelates of the examples in the blue range have a higher remission so that optinally no discoloration can be found.

The avoidance of discoloration for printing inks by titanium chelates under the invention makes possible the addition of chelates also in such cases and bigger quantities where the users of printing inks could not tolerate TiACA hitherto.

The printing inks for which the titanium chelate solutions are used, are the usual printing inks on the basis of resins such as nitrocellulose or other cellulose ester derivatives, crosslinking and hardening by addition of modified titanium acid esters and the adhesion of which on polymer substrate by addition of modified titanates is improved. The novel titanium chelate solutions no longer or only in a neglible extent have the disadvantages of titanium acetyl acetonate solutions indicated at the beginning.

The substances according to Examples 1 to 4 and 9 to 11 have the following formula:

$$Ti(OR)_{4-n}(citrate)_n,$$

in which means R=—$C_2H_5$,—$C_3H_7$ or i-resp. n—$C_4H_9$, n=1 or 2 and citrate the radicals of dialkylcitrate or monoalkylcitrate with alkyl=R.

EXAMPLE 1

Preparation of diethylcitrate-(2:1)-titanium chelate from ethyl titanate:

446.4 gm (1.8 mols) of diethylcitrate were placed into a 1000-ml round-bottom flask which was provided with a stirrer, a thermometer, a dropping funnel and a condenser, and heated to 80° C.

Thereafter, 205.2 gm (0.9 mol) of ethyl titanate were added dropwise over a period of about 5 hours. After all of the titanate had been added, the mixture was stirred for 30 minutes more at 80° C.

A light yellow liquid with the following characteristic values was obtained:

| | |
|---|---|
| Index of refraction | about 1.46 |
| Density (20° C.) | about 1.1 gm/ml |
| Viscosity | about 100 mPa.s |
| Titanium dioxide content | about 11.0% $TiO_2$ |
| Solubility | |
| water | <0.5% |
| in isopropanol | ⎫ |
| in ethyl acetate | ⎪ 10% solutions are stable |
| in methyl ethyl ketone | ⎬ without changes over a |
| in toluene | ⎪ period of more than 4 weeks |
| in methylene chloride | ⎭ |
| in heptane | 10% insoluble (forms a bottom deposit) |

Fro the above mixture 2 mol ethanol per mol titanium chelate (at 30° C. and diminished pressure) were removed.

Analysis found: 45,6% C. 6,6% H 12,3% Ti.
Calculated: 45,6% C. 6,3% H 12,6% Ti.

For the calculation the chelate was used with two groups of $C_2H_5O$ and two residues of the diethylcitrate per mol of Ti of the formula $C_{24}H_{40}O_{16}Ti$.

| | |
|---|---|
| Index of refraction $n_D^{20}$ | 1,49 |
| Density 20° C. | 1,24 gm/ml |
| Viscosity (20° C.) | 8100 mPa.s |

EXAMPLE 2

Preparation of diethyl citrate—(2:1)-titanium-chelate from isopropyl titanate:

421.6 gm (1.7 mol) of diethyl citrate were placed into a 1000-ml round-bottom flask equipped with a stirrer, a thermometer, a dropping funnel and a condenser, and hold at 20° C.

Thereafter, 241.4 gm (0.85 mol) of isopropyl titanate were added dropwise over a period of about 3.5 hours. After all of the titanate had been added the mixture was stirred for 30 minutes more at 20° C.

A light yellow liquid with the following characteristic values was obtained:

| | |
|---|---|
| Index of refraction $n_D^{20}$ | about 1.47 |
| Density (20° C.) | about 1.1 gm/ml |
| Viscosity | about 500 mPa.s |
| Titanium dioxide content | about 10.3% $TiO_2$ |
| Solubility | |
| in water | <0.5% |
| in isopropanol | ⎫ |
| in ethyl acetate | ⎪ 10% solutions are stable |
| in methyl ethyl ketone | ⎬ without change for more |
| in toluene | ⎪ than 4 weeks |
| in methylene chloride | ⎭ |
| in heptane | mixture in ratio 1:9 forms two layers. |

From the above mixture 2 mol isopropanol per mol of titanium-chelate (at 30° C. and diminished pressure) were removed.

Analysis found: 47,1% C. 6.7% H 12.3% Ti. Calculated: 47.3% C. 6.7% H 12.1% Ti.

For the calculation the chelate was used with two residues of isopropyl and two residues of teh diethylcitrate per Ti of the formula $C_{26}H_{44}O_{16}Ti$.

| | |
|---|---|
| Index of refraction $n_D^{20}$ | 1,49 |
| Density 20° C. | 1,23 gm/ml |
| Viscosity (20° C.) | 22300 mPa.s |

EXAMPLE 3

Preparation of diethyl citrate—(2:1)-titanium-chelate from butyl titanate:

396.8 gm (1.6 mol) of diethyl citrate were placed into a 1000-ml round-bottom flask equipped with a stirrer, thermometer, dropping funnel and condenser, and the contents were heated to 80° C.

Thereafter, 272 gm (0.8 mol) of butyl titanate were added dropwise over a period of about 1.5 hours. After all of the titanate had been added the mixture was stirred for 30 minutes more at 80° C.

An orange-yellow liquid with the following characteristic values was obtained:

| | |
|---|---|
| Refractive index $n_D^{20}$ | about 1.48 |
| Density (20° C.) | about 1.1 gm/ml |
| Viscosity | about 140 mPa.S |
| Titanium dioxide content | about 9.6% $TiO_2$ |
| Solubility | |
| in water | <0.5% |
| in isopropanol | |
| in ethyl acetate | 10% solutions are stable |

-continued

| | |
|---|---|
| in methyl ethyl ketone | |
| in toluene | without change for more than 4 weeks |
| in methylene chloride | |
| in heptane | |

From the above mixture 2 mol n-butanol per mol titanium chelate (at 30° C. and diminished pressure) were removed.

Analysis found: 48,9% C. 7,1% H 11,8% Ti.
Calculated 48.8% C. 7.0% H 11.6% Ti.

For the calculation the chelate was used with two n-butyl-residues and two residues of the diethylcitrate per Ti of the formula $C_{28}H_{48}O_{16}$ Ti.

| | |
|---|---|
| Index of refraction $n_D^{20}$ | 1,50 |
| Density 20° C. | 1,19 gm/ml |
| Viscosity (20° C.) | 7050 mPa.s |

EXAMPLE 4

Preparation of diethyl citrate—(1:1)-titanium chelate from butyl titanate:

248 gm (1.0 mol) of diethyl citrate were placed into a 1000-ml round-bottom flask equipped with a stirrer, a thermometer, a dropping funnel and a condenser, and the contents were heated to 80° C.

Thereafter, 340 gm (1.0 mol) of butyl titanate were added dropwise over a period of about 1.5 hours. After all of the titanate had been added, the mixture was stirred for 30 minutes more at 80° C.

An orange-yellow liquid with the following characteristics values was obtained:

| | |
|---|---|
| Refractive index $n_D^{20}$ | about 1.48 |
| Density: (20° C.) | about 1.06 gm/ml |
| Viscosity | about 120 mPa.s |
| Titanium dioxide content | about 13.6% $TiO_2$ |
| Solubility | |
| in water | <0.5% |
| in isopropanol | |
| in ethyl acetate | |
| in methyl ethyl ketone | 10% solutions are stable without change for more than 4 weeks |
| in toluene | |
| in methyle chloride | |
| in heptane | |

From the above mixture 3 mols n-butanol per mol titanium chelate (at 30° C. and diminished pressure) were removed.

Analysis found: 51.4% C. 8.2% H 15.8% Ti.
Calculated: 51.4% C. 8.2% H 15.6% Ti.

For the calculation the chelate was used with three n-butoxy-residues and one residue of the diethylcitrate per Ti of the formula $C_{22}H_{42}O_{10}$ Ti.

| | |
|---|---|
| Index of refraction $n_D^{20}$ | 1,50 |
| Density 20° C. | 1,13 gm/ml |
| Viscosity (20° C.) | 1300 mPa.s |

EXAMPLE 5

Description of the adhesion promoting affect of the products according to examples 1 to 3 in a nitrocellulose printing ink on polypropylene:

A nitrocellulose printing ink which contained 25% nitro cellulose of the Norm-type 34E dissolved in ethanol-ethyl acetate and titanium dioxide as the white pigment, was admixed with 4% by weight of the titanium chelate complexes obtained in accordance with the present invention in Examples 1 to 3 (see table below), and the mixture was stirred for a few minutes. The thus modified printing ink was applied by means of a film spreading spiral with a wet layer thickness of 12 μm to a corona-pretreated polypropylene foil, air-dried for 15 minutes, and then dried for 1 minute at 60° C. in a drying chamber with circulating air. Thereafter, the adhesion of the printing ink on the poly-propylene foil was determined by means of the adhesive tape tear-off test:

A strip of adhesive tape (for example Scotch tape) was applied to an area of about 4 cm$^2$ of dried printing ink, and the adhesive tape was pulled off again in one quick motion.

TABLE of Results

| Additive | | Amount of printing ink layer torn off in % |
|---|---|---|
| According to Example 1 | (from ethyl titanate) | about 5% |
| According to Example 2 | (from isopropyltitanate) | about 2% |
| According to Example 3 | (from butyl titante) | about 5% |
| Titanium acetylacetonate | (as a comparison) | about 5% |

The comparison with the titanium acetylacetonate was performed in the like manner with like amounts.

In comparison with TiACA the same or better quality (Example 2) adhesion was performed.

EXAMPLE 6

Test of the reaction of the titanium chelate complexes according to the invention with antioxidants:

Upon admixture of butyl hydroxyanisole (BHA) solutions with titanium acetylacetonate solutions a strong discoloration occurs. Since compounds such as BHA are also contained as antioxidants in various foils which are to be imprinted with printing inks, the reaction of solutions of the products according to the invention with a BHA solution, with BHT (2.6-di-tert.butyl-p-cresol), with HY (hydroquinone) and with MP (4-methoxyphenol).

The disocoloration is substantially less, so that the chances of yellowing in printing of foils with printing inks which contain the products according to the present invention must also be considered as significantly less.

TABLE of Results (mixture of 1% solutions in isopropanol)

| Additive | Color number according to Gardner | | | |
|---|---|---|---|---|
| | BHA | BHT | HY | MP |
| Titanium acetylacetonate | 11 | 3–4 | 10 | 8 |
| Titanium complex according to Example 1 | 3 | 2 | 6 | 4 |
| Titanium complex according to Example 2 | 2 | 2 | 6 | 4 |
| Titanium complex according to Example 3 | 3 | 2 | 5 | 4 |

By this discoloration caused by antioxidants of the titanium chelates under the invention are considerably less than by TiACA.

EXAMPLE 7

Viscosity behavior of a nitrocellulose printing ink after addition of the titanium chelate complexes according to the invention:

A white printing ink which contained 25% of an ester-soluble nitrocellulose, to which 4% of the substance to be tested had been added, served as the test medium. The viscosity was determined at intervals with a reaction viscosimeter and the printing ink was stored at 50° C. during the intervals between the viscosity measurements.

TABLE of Results

| Additive | Viscosity in mPa.s after storage period at 50° C. | | | | |
|---|---|---|---|---|---|
| | 1 day | 1 week | 2 weeks | 1 month | 2 months |
| Titanium acetyl acetonate | 560 | 480 | 480 | 440 | 850 |
| Titanium chelate complex of Example 2 | 600 | 470 | 460 | 530 | 900 |

EXAMPLE 8

Remission diagrams of white antioxidants containing printing ink in dependence on the added additive: A nitrocellulose printing ink containing 25 wt.-% of nitrocellulose of the norm type 34E, solved in ethanol ethylacetate, titanium dioxide as white pigment and additionally 1 wt.-% butyl hydroxyanisol (BHA) as antioxidant, one time without any further addition and one time with an addition of 4 wt.-% TiACA and then with other additives of each 4% titanium chelate according to Examples 1–3 with the foil drawing up spiral is torn in a wet layer thickness of 36μm is on polypropylene foils. After drying in a color measuring apparatus Datacolor 3890 tests are made with respect to remission.

Depending on the wave length λ (nm) of the radiated light the following remission values (in %) are obtained).

| White ink with 1% BHA-addition | Remission bei λ = | | | | | |
|---|---|---|---|---|---|---|
| | 400 nm | 450 nm | 500 nm | 550 nm | 600 nm | 700 nm |
| without additive | 60 | 77 | 78 | 79 | 80 | 79 |
| with 4% TiACA | 13 | 17 | 30 | 56 | 73 | 78 |
| with 4% Titaniumchelate (Ex. 1) | 45 | 58 | 65 | 73 | 74 | 75 |
| with 4% Titaniumchelate (Ex. 2) | 44 | 57 | 66 | 74 | 77 | 77 |
| with 4% Titaniumchelate (Ex. 3) | 48 | 62 | 70 | 77 | 79 | 79 |

While by addition of BHA alone no discoloration is obtained, the additional feed of titanium acetyl acetonate results into a color of deep orange, but by the addition to titanium chelates under the invention only a scarcely discoloration to yellowish is received.

EXAMPLES 9 to 11

Examples 1 to 4 were repeated, at which, however 2 mols of monoethylcitrate with 1 mol tetraethyl titanate (Example 9), 2 mols monoethylcitrate with 1 mol tetrabutyltitanate (Example 10) and 1 mol monoethylcitrate with 1 mol tetraethyltitanate (Example 11) at 80° C. are used.

There obtained bis-(monoethylcitrate)-diethyltitanate (Example 9).

Bis-(monoethylcitrate)-dibutyltitanate (Example 10)

Monoethylcitrate-triethyl-titanate (Example 11) in solution of that alcohol which was released during the reaction. Evaporation of the alcohol as in Examples 1 to 4 and the elementary analysis of the residue confirmed the corresponding formulas and the calculated molecular weights.

We claim:

1. A titanium chelate of the formula:

$$Ti(OR)_{4-n}(citrate)_n$$

wherein
R is ethyl, propyl, isobutyl or butyl,
n is 1 or 2, and
citrate is the radical of a monoalkyl or dialkyl citrate, the alkyl moiety of which is ethyl, propyl, isobutyl or butyl.

2. A solution of a titanium chelate of the formula $$Ti(OR)_{4-n}(citrate)_{n:ps}$$

wherein
R is ethyl, propyl, isobutyl or butyl,
n is 1 or 2, and
citrate is the radical of a monoalkyl or dialkyl citrate, the alkyl moiety of which is ethyl, propyl, isobutyl or butyl in an alkanol of the formula

ROH wherein R has the meanings previously defined and is identical to R in said titanium chelate.

3. The method of preparing a titanium chelate of claim 1, which comprises reacting a tetraalkyl titanate with a citric acid dialkyl ester, and distilling off the alcohol liberated by the reaction.

4. The method of preparing an alkanolic solution of claim 2, which comprises reacting a tetraalkyl titanate with a citric acid dialkyl ester at a temperature between 20° and 100° C., and evaporating the alcohol in the reaction mixture to the desired alcohol content.

5. A printing ink composition comprising a printing ink and a titanium chelate solution of claim 2.

* * * * *